| (12) United States Patent | (10) Patent No.: US 11,890,363 B2 |
| Sakuma et al. | (45) Date of Patent: Feb. 6, 2024 |

(54) LIQUID COSMETIC COMPOSITION

(71) Applicant: MITSUBISHI PENCIL COMPANY, LIMITED, Shinagawa-ku (JP)

(72) Inventors: Satoshi Sakuma, Fujioka (JP); Yuichi Yamazaki, Fujioka (JP)

(73) Assignee: MITSUBISHI PENCIL COMPANY, LIMITED, Shinagawa-ku (JP)

( * ) Notice: Subject to any disclaimer, the term of this patent is extended or adjusted under 35 U.S.C. 154(b) by 166 days.

(21) Appl. No.: 17/625,521

(22) PCT Filed: Jul. 8, 2020

(86) PCT No.: PCT/JP2020/026671
§ 371 (c)(1),
(2) Date: Jan. 7, 2022

(87) PCT Pub. No.: WO2021/006289
PCT Pub. Date: Jan. 14, 2021

(65) Prior Publication Data
US 2022/0265534 A1    Aug. 25, 2022

(30) Foreign Application Priority Data

Jul. 10, 2019   (JP) .................................. 2019-128295

(51) Int. Cl.
*A61K 8/25* (2006.01)
*A61K 8/02* (2006.01)
(Continued)

(52) U.S. Cl.
CPC .............. *A61K 8/25* (2013.01); *A45D 34/042* (2013.01); *A61K 8/0254* (2013.01); *A61K 8/26* (2013.01);
(Continued)

(58) Field of Classification Search
CPC .......... A61K 8/25; A61K 8/0254; A61K 8/26; A61K 8/731; A61K 8/736; A61K 2800/43;
(Continued)

(56) References Cited

U.S. PATENT DOCUMENTS 5,478,550 A * 12/1995 Suzuki ..................... A61K 8/19
424/59
2003/0017123 A1    1/2003 Scancarella et al.
(Continued)

FOREIGN PATENT DOCUMENTS

JP          7-138131 A      5/1995
JP       2001-187716 A      7/2001
(Continued)

OTHER PUBLICATIONS

Extended European search report in PCT/JP2020026671 dated Sep. 26, 2023.
(Continued)

*Primary Examiner* — David J Walczak
(74) *Attorney, Agent, or Firm* — Oblon, McClelland, Maier & Neustadt, L.L.P.

(57) ABSTRACT

A liquid cosmetic composition which provides easily a clear and brilliant coating film without causing flaky pigments to be overlapped on each other when the liquid cosmetic composition containing a small amount of brilliant flaky pigments is filled in an applicator having a coating part composed of a brush to be coated on a surface such as a skin. The liquid cosmetic composition of the present invention is characterized in containing at least 0.01 to 10 mass % of a flaky pigment coated on a surface with a compound selected from the following A group, 0.05 to 5 mass % of layered clay mineral particles, 1 to 20 mass % of an acrylic copolymer in terms of a solid content and water and being filled in an applicator provided with a coating part having a brush:
A group: cellulose, hemicellulose, lignin, chitin, chitosan.

4 Claims, 3 Drawing Sheets

(51) Int. Cl.
  *A61K 8/26* (2006.01)
  *A61K 8/73* (2006.01)
  *A45D 34/04* (2006.01)
  *A61Q 1/10* (2006.01)
(52) U.S. Cl.
  CPC .............. *A61K 8/731* (2013.01); *A61K 8/736* (2013.01); *A61Q 1/10* (2013.01); *A61K 2800/43* (2013.01); *A61K 2800/48* (2013.01); *A61K 2800/87* (2013.01)
(58) Field of Classification Search
  CPC ............ A61K 2800/48; A61K 2800/87; A45D 34/042; A61Q 1/10
  USPC ....... 424/59, 401; 106/491, 14.05, 482, 480, 106/479, 483; 427/205
  See application file for complete search history.

(56) References Cited

U.S. PATENT DOCUMENTS

| | | |
|---|---|---|
| 2007/0181038 A1 | 8/2007 | Sabesan et al. |
| 2009/0175813 A1 | 7/2009 | Morita et al. |
| 2011/0110995 A1 | 5/2011 | Hasegawa et al. |
| 2012/0128748 A1 | 5/2012 | Nagata et al. |
| 2013/0143047 A1 | 6/2013 | Schwarte et al. |
| 2014/0020702 A1 | 1/2014 | Eguchi et al. |
| 2018/0369081 A1 | 12/2018 | Sakuma et al. |

FOREIGN PATENT DOCUMENTS

| | | |
|---|---|---|
| JP | 2004-238366 A | 8/2004 |
| JP | 2005-187397 A | 7/2005 |
| JP | 2011-51972 A | 3/2011 |
| JP | 2013-124227 A | 6/2013 |
| JP | 2014-65700 A | 4/2014 |
| JP | 2014-144923 A | 8/2014 |
| JP | 2015-193543 A | 11/2015 |
| JP | 2016-41674 A | 3/2016 |
| JP | 2017-114803 A | 6/2017 |
| JP | 2017-114825 A | 6/2017 |
| WO | WO 2007/123115 A1 | 11/2007 |
| WO | WO 2009/142047 A1 | 11/2009 |

OTHER PUBLICATIONS

International Search Report dated Sep. 15, 2020 in PCT/JP2020/026671 filed on Jul. 8, 2020 (3 pages).

* cited by examiner (a)

(b)

LIQUID COSMETIC COMPOSITION

TECHNICAL FIELD

The present specification relates to a liquid cosmetic composition containing a flaky pigment exhibiting brilliance, and more specifically to a liquid cosmetic composition which provides easily a clear and brilliant coating film, when the liquid cosmetic composition containing a small amount of flaky pigments is filled in an applicator provided with a coating part having a brush and applied on a face to be coated such as a skin or eyebrows, it is spread on the face to be coated without making the flaky pigments overlapped.

BACKGROUND ART

In a liquid cosmetic composition to form a brilliant coating film on a face to be coated such as a skin and eyebrows, conventionally, flaky pigments (brilliant pigments) exhibiting brilliance are usually contained therein.

However, the flaky pigments have a large particle size and are easily settled down in a liquid, and they are readily overlapped on each other in a layer manner when once settled down so that they are adhered and overlapped on each other to produce a hard cake. A layered structure is difficult to be peeled again and difficult to be redispersed in the liquid.

Then, known as an aqueous makeup cosmetic containing brilliant powder are aqueous liquid cosmetic compositions. They are not only improved in dispersion stability of brilliant powder and the like to be prevented from aggregation during storage and drainage but also excellent in color development and glossy feeling and in spreadability and adhesive property by adding an aqueous alkali thickening type polymer emulsion, a pigment such as carbon black, a brilliant powder, an ethanol-soluble type film forming agent, and alkali (refer to, for example, a patent document 1).

In a prescription of the patent document 1, as a large amount of a basic compound is added to make a vehicle highly viscous to prevent it from being turned into a layered hard cake, when the liquid turns to an acidity with the passage of time, it may become unstable. Further, the aqueous liquid cosmetic composition is highly viscous originally in the liquid itself, so that a problem that a coating means is limited has been involved therein.

The present inventors provide as a prescription other than the patent document 1 described above, a prescription of an aqueous liquid cosmetic which is slightly low viscous using an aqueous emulsion of an acrylic acid polymer having specific properties and fermented cellulose and which prevents a brilliant pigment from settling down (color separation in a coating part) and can be coated even when it is filled in an applicator provided with a brush as a coating part (refer to, for example, a patent document 2).

In the above prescriptions and the like, the compositions are as slightly viscous as some ten to some hundred mPa·s, though not very viscous. Further, the present applicant provides as another method, a method in which a surface of a flaky pigment is covered with a water-insoluble substance to prevent a hard cake from being produced (refer to, for example, a patent document 3).

However, also either of the prescriptions of the patent documents 2 and 3 described above is restricted in coating means in the event due to a high viscosity, and even though a large amount of brilliant pigments is added, the brilliant pigments are overlapped on each other after coating in some cases. In these cases, clear brilliant coating films are hardly obtained in spite of adding them at large amounts.

On the other hand, it is disclosed that a liquid cosmetic for a brush pen type cosmetic containing hydrophilically treated black iron oxide, hydrophilic nonionic surfactant, polysaccharides, a metal ion blocking agent and a polymer emulsion is good in dispersion with the passage of time, easy coating, excellent usability such as coloring, makeup durability and the like, excellent in a discharge property (clogging) of the brush pen type cosmetic, can be blended particularly with pearl pigments, and provides stable redispersibility, dischargeability, and satisfactory pearl effect (refer to, for example, a patent document 4). Further, it is described in the patent document 4 that pigment stability with the passage of time and a discharge property of the filled liquid cosmetic from the brush are more improved by further adding a water-swelling clay mineral.

However, a principal purpose of the liquid cosmetic for the brush pen type cosmetic described in the patent document 4 is to improve dispersibility of black iron oxide with the passage of time when blending the black iron as a coloring pigment, and it is not specifically referred whether or not a satisfactory "pearl effect" is obtained when an amount of the pearl pigment is small.

Incidentally, it is disclosed as a method for exhibiting excellent brilliance in a prescription containing a brilliant pigment, to fill a cosmetic applicator with a power solid cosmetic prepared by combining a brilliant flaky pigment, talc having a specific collapse index and an oily ingredient so that the powder is caused to be suitably collapsed when it has moved to a cosmetic tool, whereby the powder containing brilliant powder is spread evenly on a skin when it is applied from the cosmetic applicator on the skin, and diffused reflection of light incident into the brilliant powder is decreased very much and close to regular reflection, so that excellent brilliant feeling is recognized (refer to, for example, a patent document 5).

However, the above prescription is referred to the powder solid cosmetic to make it possible to achieve it because the powders themselves are adhered without moving until coated. In particular, a blend amount of the brilliant pigment is large as much as 50 to 80 weight %, and the present invention is different in a technical idea.

PRIOR ART DOCUMENTS

Patent Documents

Patent document 1: JP-A2017-114803 (claims, paragraph 0007 and the like)
Patent document 2: JP-A2017-114825 (claims, paragraph 0011 and the like)
Patent document 3: JP-A 2013-124227 (claims, and the like)
Patent document 4: JP-A 2005-187397 (claims, paragraphs 0041, 0047 and the like)
Patent document 5: JP-A2004-238366 (claims, paragraph 0020 and the like)

DISCLOSURE OF THE INVENTION

The present disclosure intends to solve the conventional problems described above, and an object thereof is to provide a liquid cosmetic composition which provides easily a clear and brilliant coating film without causing flaky pigments to be overlapped on each other when a liquid cosmetic composition containing a small amount of brilliant flaky pigments to coat it on a surface to be coated such as a skin is filled in an applicator having a painting part composed of a brush.

Intense investigations done by the present inventors have resulted in finding that the liquid cosmetic composition which meets the object described above is obtained by adding at least a flaky pigment coated with a compound having specific physical properties, layered clay mineral particles, an acrylic copolymer and water respectively in specific ranges and filling it in an applicator provided with a coating part composed of a brush. Thus, they have come to complete the present invention.

That is, the liquid cosmetic composition of the present invention is characterized in containing at least 0.01 to 10 mass % of a flaky pigment coated on a surface with a compound selected from the following A group, 0.05 to 5 mass % of layered clay mineral particles, 1 to 20 mass % in terms of a solid content of an acrylic copolymer and water and being filled in an applicator having a coating part composed of a brush.

A group: cellulose, hemicellulose, lignin, chitin, chitosan.

Further, the cosmetic composition described above contains preferably a thickener.

The flaky pigment described above is preferably an aluminum flake pigment.

The layered clay mineral particles are preferably layered silicate mineral particles.

According to the present disclosure, provided is a liquid cosmetic composition which provides easily a clear and brilliant coating film without causing flaky pigments to be overlapped on each other when an applicator having a coating part composed of a brush is filled with the liquid cosmetic composition containing a small amount of brilliant flaky pigments to coat it on a surface to be coated such as a skin.

In the present specification, both the general descriptions described above and detailed descriptions described later are exemplary and explanatory and shall not restrict the present invention described in the claims.

MODE FOR CARRYING OUT THE INVENTION

Figure 1:
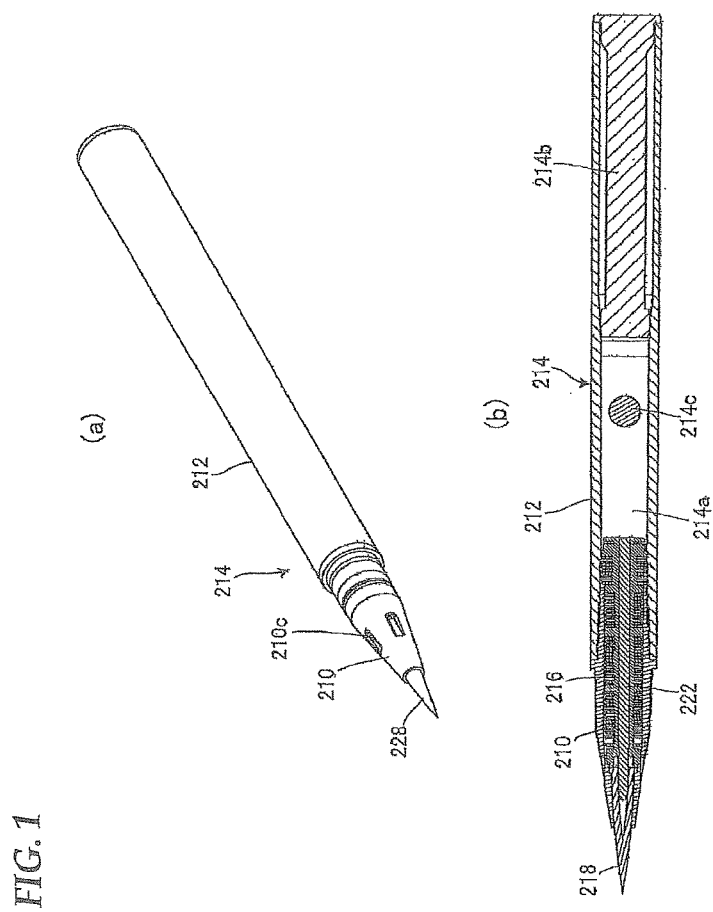
FIGS. 1(a) and (b) is a drawing showing one example of the embodiment of an applicator filled with the liquid cosmetic composition of the present invention.

At least several embodiments of the present invention shall be explained below in detail.

The liquid cosmetic composition of the present invention is characterized in containing 0.01 to 10 mass % of a flaky pigment coated on a surface with at least a compound selected from the following A group, 0.05 to 5 mass % of layered clay mineral particles, 1 to 20 mass % of an acrylic copolymer in terms of a solid content and water and being filled in an applicator having a coating part composed of a brush.

A group: cellulose, hemicellulose, lignin, chitin, chitosan.

The flaky pigment used in the present disclosure is a flaky pigment which is brilliant and coated on a surface with at least a compound selected from the foregoing A group. An example is a flaky pigment such as a pearl pigment, an aluminum flake pigment (aluminum powder pigment), a metal or metal oxide coating glass flake and an aluminum-coating polyester film, coated on a surface with a compound selected from the forgoing A group.

At least one (alone or combination of two or more kinds thereof respectively; hereinafter the same shall apply) selected from cellulose which is a polymer (oxidized cellulose, fermented cellulose and the like), hemicellulose, lignin, chitin and chitosan can be used for the compound selected from the A group described above.

A method for coating the above compound on a surface of the flaky pigment described above includes, for example, 1) a method in which an aqueous slurry prepared by mixing at least one compound selected from the A group described above and the flaky pigment is sprayed and dried by means of a spray dryer to let the compound selected from the A group described above adhere on a surface of the flaky pigment (hereinafter, referred to as "production method 1"), 2) a method in which a substance soluble in an acidic or basic aqueous solution is dissolved in water adjusted in pH and in which pH of the solution is shifted to insolubilization by adding acid or base to precipitate at least one compound selected from the A group on a surface of the flaky pigment (hereinafter, referred to as "production method 2").

If a surface coating amount of the compound selected from the A group described above is too small, an effect of redispersibility by inhibition of a hard cake is not obtained, and on the other hand, if it is too large, not only pearl feeling (brilliance) is reduced, but also a pearl surface does not become point contact and becomes face contact, so that the effect of redispersibility is not obtained. Accordingly, the surface coating amount (calculated from mass % in surface treatment) of the compound selected from the A group desirably falls in a range of 0.1 to 10%, preferably 0.5 to 8% and more preferably 1 to 7% in terms of a surface coating rate of the flaky pigment (calculated from mass % in surface treatment).

To be specific, the flaky pigment which can be used include, for example, compounds prepared by coating flaky pigments such as commercially available aluminum flake pigments, metal oxide-coated glass flakes (brand name "Metashine" and the like), metal oxide-coated mica (brand name "Lumina" and the like) on surfaces with the compound selected from the A group described above. Further, if commercial products coated on surfaces with the compound selected from the A group described above are available, they can be used.

When the used coated flaky pigment having a larger particle diameter of a flat surface is used, brilliant feeling is higher. From the viewpoint of suitably exhibiting the effect of the present invention, the particle diameter is preferably 5 μm to 100 μm.

In the present disclosure (including examples), "a particle diameter" or "an average particle diameter" described later means a value measured and calculated by a dynamic light scattering method (Particle diameter analyzer FPAR-1000, manufactured by Otsuka Electronics Co., Ltd.).

Crystals of the compound described above can be confirmed on a surface observed under an electronic microscope (×35000 magnifications) in the flaky pigment coated with the compound selected from the A group described above used in the present invention.

The flaky pigment coated with the compound selected from the A group described above in the present invention and a flaky pigment which is not coated with it can be distinguished in such a manner that redispersibility is not obtained in a system where a non-coated flaky pigment is blended while good redispersibility is obtained in a system where the flaky pigment coated with the compound selected from the A group is used.

In the present disclosure, a content of the flaky pigment coated with the compound selected from the A group is preferably 0.01 to 10% by mass (hereinafter, % by mass is referred to merely as %), more preferably 0.5 to 5% in terms of a whole amount of the composition in order to obtain satisfactory brilliance and concealment in using the product.

If the content of the flaky pigment coated therewith is less than 0.01%, brilliance is poor. On the other hand, if it exceeds 10%, the flaky pigment is increased in a concentration and brilliance and expensiveness increase naturally, which results in reduction in significance to have the constitution of the present invention. Further, it is likely to result in reduction in a coating property or inferior coating by continuous coating and therefore is not preferred. Incidentally, hard caking is expedited in non-surface treated flaky pigment.

The layered clay mineral particles used in the present disclosure are added in order to exhibit well the effects of the present invention in a state where it is difficult for the flaky pigments to come in contact each other while layered clay mineral particles are interposed between the flaky pigments in the composition.

The usable layered clay mineral particles include crystalline inorganic compounds having layered structures represented by layered silicate minerals. The layered clay mineral particles may be natural substances and artificially produced substances.

To be specific, the layered silicate mineral particles represented by a kaolinite group, a smectite group, a mica group and the like can be included. Clay mineral particles of the kaolinite group include, for example, kaolinite. Clay mineral particles of the smectite group include, for example, montmorillonite, bentonite, saponite, hectorite, pyderite, stevencite and nontronite. Clay mineral particles of the mica group include, for example, vermiculite, halloysite and tetrasilisic mica. In addition thereto, hydrotalcite which is layered double hydroxide can be used as well.

Particularly, the smectite group out of the layered clay mineral particles described above is considered to inhibit well contact of the flaky pigments themselves in an aqueous state and suitably used from the view point of enhancing brilliant feeling and inhibiting upper and lower difference. Commercially available products such as Kunipia-F, Sumecton-SWN, Sumecton-SA (manufactured by Kunimine Industries Co., Ltd.), Venger FW (manufactured by HOJUN Co., Ltd.) and the like can be used.

At least one (alone or combination of two or more kinds) of these layered clay mineral particles can be used.

These layered clay mineral particles have an average particle diameter of preferably 50 nm or more, more preferably 100 nm or more and preferably 1000 nm or less, more preferably 700 nm or less. To be specific, the layered clay mineral particles have an average particle diameter of preferably 50 nm or more and 1000 nm or less, more preferably 100 nm or more and 700 nm or less. When the layered clay mineral particles are flaky, an average particle diameter of the mineral shows a length of the longest side. A dispersibility in the composition can be improved by using the layered clay mineral particles having an average particle diameter falling in the range described above, which results in making it possible to further improve a non-contact property of the flaky pigment. The layered clay mineral particles may be further crushed by a crushing device in order to cause the average particle diameter of the layered clay mineral particles to fall in the ranges described above.

A content of the layered clay mineral particles is preferably 0.05 to 5%, more preferably 0.1 to 3% from the viewpoints of providing a good brilliant feeling and improving as well a thickening effect even in a small amount of the flaky pigment.

If the content of the layered clay mineral particles is less than 0.05%, it is difficult to exhibit the effects of the present invention. On the other hand, if it exceeds 5%, a thickening action becomes notable, then a discharge property from a coating part, good coating and the like are lost.

The acrylic copolymer is used in the liquid cosmetic composition of the present invention from the viewpoints of a sticking property and a dispersion stability.

The used acrylic copolymer includes, for example, at least one of alkyl acrylate copolymers, acrylate copolymers, acrylate copolymer ammonium, acrylic resin alkanolamine solutions, alkyl acrylates •vinyl acetate copolymers, (alkyl acrylate/octylacrylamide) copolymers, silicone-modified acrylic copolymers, octylamide acrylate •acrylic acid copolymers.

In particular, the acrylic copolymer used in the present invention is preferably the alkyl acrylate copolymer or the acrylate copolymer from the viewpoint of further exhibiting the effects of the present invention.

The alkyl acrylate copolymer includes, for example, an (octylacrylamide/hydroxypropyl acrylate/butylaminoethyl methacrylate) copolymer (brand name "Amphomer": powder), alkyl acrylate copolymer ammonium (brand name "Yodosol GH800F": solid content 45%) and the like.

2-Amino-2-methyl-1-propanol, 2-amino-2-methyl-1,3-propanediol, triethanolamine, L-arginine, aqueous ammonia, sodium hydroxide and the like can be used for neutralization. 2-Amino-2-methyl-1-propanol is particularly preferred.

A content of these acrylic copolymers is preferably 1 to 20%, more preferably 1 to 10% based on a whole amount of the composition in terms of a solid content.

If the content of the acrylic copolymer is less than 1%, it is difficult to exhibit the effects of the present invention. On the other hand, if it exceeds 20%, a thickening action becomes notable to make it difficult to carry out discharge from the coating part, good coating and the like.

A thickening agent may be contained in the liquid cosmetic composition of the present invention from the viewpoints of a coating property, a storage stability and further inhibition of settling down the flaky pigment described above.

The usable thickening agent is preferably used, as described later, in order to optimize a viscosity of the liquid cosmetic composition and exhibit the addition effect described above and includes, for example, at least one of crystalline cellulose, dextrin, xanthan gum, cellulose, hydroxyethylcellulose, gellan gum, guar gum and the like. Among them, crystalline cellulose and xanthan gum are preferably used from the viewpoints of an optimal viscosity and further improving the upper and lower difference.

A commercially available product of the usable thickening agent include, for example in a case of the crystalline cellulose, products comprising a colloidal grade in which a surface of fine cellulose crystal body is subjected to coating treatment with a water-soluble polymer and the like, and a specific example thereof includes Ceolus RC-591, RC-N81, RC-591NF, CL-611, Ceolus Cream (all, manufactured by Asahi Kasei Corporation), and in a case of the xanthan gum, Keltrol (manufactured by DSP GOKYO FOOD & CHEMI- CAL Co., Ltd.), Labor Gum GS-C (manufactured by DSP GOKYO FOOD & CHEMICAL co., Ltd.) and the like.

A content of the thickening agent in the present invention is, as described later, a content for the liquid cosmetic composition to exhibit the effects of the present invention by adjusting a viscosity to a viscosity range and is adjusted in an optimum amount to a whole amount of the liquid cosmetic composition.

In the liquid cosmetic composition of the present invention, the remainder is adjusted by water (refined water, ion exchanged water, distilled water, purified water and the like) which is a solvent in addition to the respective components described above.

Further, a moisturizer, an antimicrobial agent, a defoaming agent, an inorganic pigment and an organic pigment, a dye, a surfactant, a water-soluble organic solvent and the like can be suitably added to the liquid cosmetic composition of the present invention in a range in which troubles are not caused on the dispersion and in which the effects of the present invention are not damaged.

The usable moisturizer includes, for example, water-soluble glycols such as 1,3-butylene glycol, 1,4-butylene glycol, pentylene glycol, ethylene glycol, diethylene glycol, polyethylene glycol, propylene glycol, dipropylene glycol, glycerin and the like.

A content of the moisturizers is used in a range of preferably 1 to 30% more preferably 5 to 20% based on a whole amount of the composition.

The usable antimicrobial agent includes parabens, sodium dehydroacetate, phenoxyethanol and the like. A preservative is included in the antimicrobial agent in the present invention, and methyl paraoxybenzoate, ethyl paraoxybenzoate, propyl paraoxybenzoate, butyl paraoxybenzoate, isopropyl paraoxybenzoate and the like can be used as the parabens which are preservatives in a suitable amount.

The usable defoaming agent includes, for example, polydimethylsiloxane (dimethicone). This polydimethylsiloxane is a silicone oil comprising a mixture of linear siloxane polymers in which terminals are blocked and methylated by trimethylsiloxane units, and KS-66 (manufactured by Shin-Etsu silicone Co., Ltd.) and the like can be used as commercial products in a suitable amount.

In the present disclosure, an organic pigment, an AL lake pigment and a dye are blended in order to obtain further clear color tone in addition to the coating-treated flaky pigment described above to make it possible to obtain a clear color development. In a case of flaky pigments which are not subjected to the coating treatment described above, hard cakes are deteriorated particularly by blending an AL lake pigment, particularly, a dye, but in a case of flaky pigments which are subjected to the coating treatment with the water-insoluble substances described above, hard cakes are not caused with the dye. The cause that AL lake pigment deteriorates the hard cakes in a case that the flaky pigments which are not subjected to the coating treatment described above are blended is that a lake dye is deviated (bled) from AL to be turned into a dye.

In the present disclosure, pH of the liquid cosmetic composition falls preferably in a range of 6 to 9 from the viewpoint of inhibiting skin stimulation. The pH can be adjusted by using a pH adjusting agent such as 2-amino-1-methyl-1-propanol, 2-amino-2-methyl-1,3-propanediol, tri-ethanolamine, L-arginine, aqueous ammonia, sodium hydroxide and the like, and the pH is adjusted particularly preferably by 2-amino-2-methyl-1-propanol.

If the liquid cosmetic composition in the present disclosure has too high viscosity, it is not discharged from a brush, and if it has too low viscosity, it is difficult to use due to blurred drawn lines. Accordingly, the viscosity preferably falls in a rage of 2 to 10 mPa·s at 25° C. at a shear rate of 383 $s^{-1}$.

The flow amount is secured by setting the respective viscosity ranges described above, and lines are not blurred and are easy to be drawn and coated.

The viscosity ranges described above can be adjusted by combining the coating-treated flaky pigment, the layered clay mineral particles, water and the acrylic copolymer each described above at optimum contents.

The liquid cosmetic composition of the present disclosure is produced by mixing and dispersing the respective components described above at optimum contents by means of, for example, a bead mill, a homomixer, a disper, an attritor, a ball mill, a sand grinder and the like.

The liquid cosmetic composition of the present disclosure can be suitably used by housing in an applicator having a coating part composed of a brush (a spike head).

In a case of an applicator equipped with a coating part comprising of a solidified resin or a so-called pen core type in which fibers are fused, the flaky pigment can be slid on a coating surface by coating but a coating liquid is scraped, so that an effect of elevating a brilliant feeling is resultingly reduced and is inferior a little in a coating property.

A usable applicator includes, for example, an applicator shown in FIG. 1, in which the liquid cosmetic composition constituted in the manner described above is stored.

A liquid cosmetic applicator mounted with the liquid cosmetic composition of the present disclosure includes an applicator of a collector type. It has, for example, a shaft body 214 in which a front shaft 210 and a shaft main body 212 at a rear part side of the front shaft 210 are fitted as shown in FIG. 1 (a), and a collector 216 formed in a comb-teeth shape of a mode in which a plurality of sheet parts are arrayed in a shaft direction at a front part of the shaft body 214, as shown in FIG. 1 (b), to store the liquid cosmetic composition (hereinafter referred to as "a coating liquid") described above in a storage space 214a at a rear part of the shaft body 214.

The shaft main body 212 at a rear part of the shaft body 214 described above is formed in a pipe shape which is communicated in an inside and opened to front and rear sides. A tail plug 214b is fitted to a rear part of the shaft main body 212 which is also the rear part of the shaft body described above to close the rear part of the shaft main body 212. A shaft body 214 inner space (which is also a shaft main body 212 inner space) which is interposed by a front end of the tail plug 214b and a rear end of the collector 216 is a storage space 214a.

In the storage space 214a, there is not arranged an impregnant body such as an inner cotton and the like but a coating liquid is stored directly therein. And a stirring body (a ball and the like) 214c for stirring the coating liquid is arranged therein.

The front shaft 210, the shaft main body 212, the collector 216, a cap and the like can be resin molded articles. A ball material made of a metal, made of a resin and the like can be used for the stirring body 214c.

The collector 216 is of a structure covered and held with the front shaft 210 and the shaft main body 212.

A coating part 218 comprising a brush body which is acuminate and assumes a tapering shape is projected from an opening of a front end part of the front shaft 210, and a cap covering the coating part 218 is of a structure detachably engaged with the front shaft 210. The front shaft 210 assumes an approximately conical side-surface shape and is formed so as to be tapered, and a tip angle of the front shaft 210 is formed preferably approximately at the same angle as a tip angle of the coating part 218.

The coating part 218 is a tapered brush part composed of resin fibers, a natural fiber bundle or a resin-made porous body. The coating part 218 is expanded in a diameter of a rear end part into a flange shape, and the part expanded in a diameter is engaged with the front shaft 210 in an inside to prevent it from coming out.

The collector 216 of a bellows shape is arranged behind a writing part 218 in an inside of the front shaft 210 which is hollow and formed so as to be tapered, and an inner core 222 is arranged through an inside of a hollow part of the collector 216. The inner core 222 can be composed of a capillary member such as a resin fiber bundle, a natural fiber bundle and a resin-made porous body.

In the inner core 222, the inner core 222 is not projected from a rear end part of the collector 216 into the storage space 214*a* of the shaft body 214 (refer to FIG. 1 (*b*)). A rear end face of the inner core 222 almost agrees with a rear end face of the collector 216. A volume of the storage space 214*a* can be secured by causing the inner core 222 to agree without causing a rear end of the inner core 222 to be projected into the storage space 214*a*. Also, the rear end of the inner core 222 is not projected into the storage space 214*a*, and therefore when the stirring body 214*c* is disposed in the storage space 214*a*, the stirring bod 214*c* does not collide against the inner core 222 even if the stirring body 214*c* moves in the storage space 214*a* to prevent the inner core 222 from being deformed, so that the coating liquid can be sufficiently impregnated.

The liquid cosmetic applicator of the configuration described above has been explained referring to examples of a liquid eyeliner or a liquid eye shadow which are the liquid cosmetic compositions of the present disclosure, but it shall not be restricted to them and can be applied to an eyebrow applicator for drawing lines on eyebrows and drawing lines on a skin.

An applicator of a rotary extension type shown in FIG. 1 has been used as a liquid pressure mechanism of the liquid cosmetic applicator of the configuration described above, however, a liquid applicator of a knock extension type may be also used.

Although the liquid cosmetic composition of the present disclosure constituted in the manner described above contains a small amount of the brilliant flaky pigment, when it is filled in an applicator having a coating part such as a brush and coated on a surface to be coated such as a skin, a clear and brilliant coating film is easily obtained without being overlapped on each other. This point is inferred to be attributable to the operation/working effect described below.

It is inferred that by use of the liquid cosmetic composition of the present disclosure layered clay mineral particles contained prevent the flaky brilliant pigments from coming in contact with themselves, and the flaky brilliant pigments have a high redispersibility due to the surface treatment subjected to the flaky brilliant pigments even when coming in contact to provide a shear force to the liquid cosmetic composition of the brush by a force caused in coating. As a result, the flaky brilliant pigments slide to provide a coating film where the flaky brilliant pigments are widely spread so that excellent brilliance is exhibited for smaller content. Accordingly, since the liquid cosmetic composition of the present disclosure has the operation/working effect described above, it can be suitably used for eye make such as eyeliners and the like.

EXAMPLES

The present invention shall be explained below in further details with reference to examples and comparative examples, but the present invention shall not be restricted by the following examples and the like.

Examples 1 to 9 and Comparative Examples 1 and 9

The ingredients were mixed and dispersed according to formulations shown in the following Table 1 and Table 2 by means of a homo mixer or a disper to prepare the respective liquid cosmetic compositions.

The respective liquid cosmetic compositions prepared in Examples 1 to 9 and Comparative Examples 1 and 9 were evaluated for pH (25° C.), a viscosity at 25° C., a brilliant feeling and upper and lower difference by the following measuring methods and evaluation methods. The results thereof are shown in the following Table 1 and Table 2.

Measuring method of pH:

The obtained respective liquid cosmetic compositions were measured for pH at a temperature of 25° C. by means of a glass electrode type pH measuring device (manufactured by HORIBA, Ltd.).

Measuring method of viscosity:

The obtained respective liquid cosmetic compositions were measured for viscosity at a temperature of 25° C. and at a predetermined shear rate (100 rpm: 383 s$^{-1}$) by means of a cone plate-type viscometer (among TV30 type viscometers, ELD type viscometer, standard cone plate manufactured by Tokimec Inc.).

Figure 2:
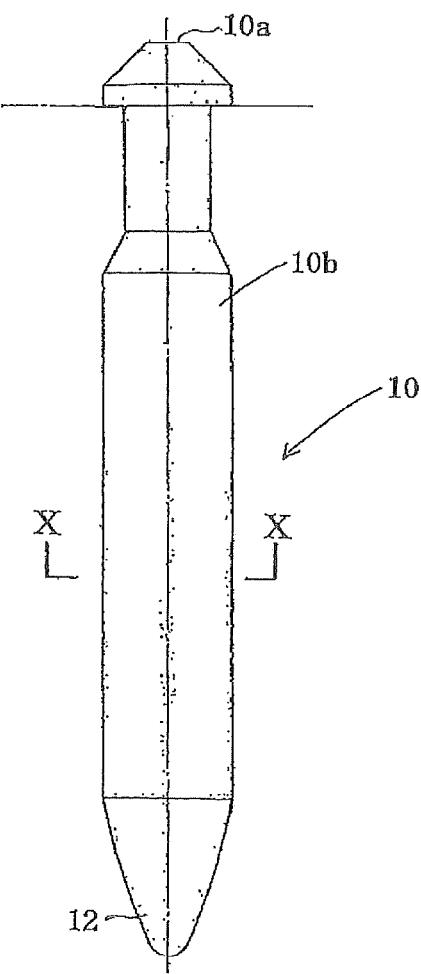
FIGS. 2 (a) and (b) are drawings showing one example of a pen type coating part used in the comparative examples; (a) is a front view, and (b) is an X-X line cross section of (a).
Figure 2:
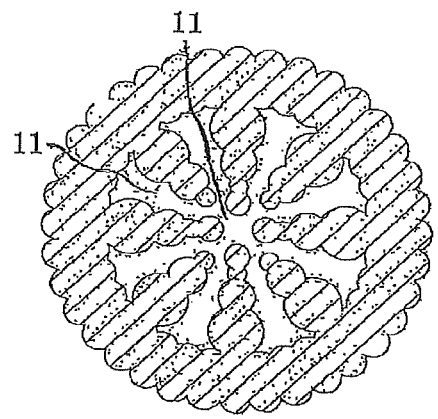
Figure 3:
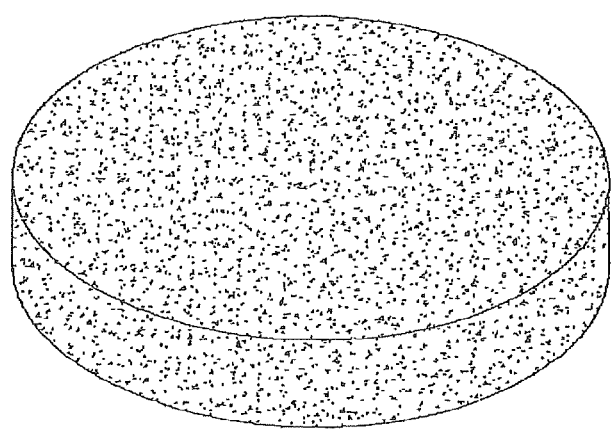
FIG. 3 is a perspective view showing one example of a puff used in the comparative examples.

Measuring method of brilliant feeling:

The cosmetic composition was spread on a skin using a brush, a pen core or a puff each shown in FIG. 1 to FIG. 3 to evaluate the brilliant feeling and the upper and lower difference by the following evaluation method.

The brush used the respective examples of FIG. 1 is an acuminate brush body (brush) composed of bundles of polyethylene terephthalate-made resin fibers having φ0.05 to 0.3 mm. The pen core used in the comparative example of FIG. 2 is obtained through a step of extrusion molding of a polyacetal resin (POM). This pen core 10 is, as shown in FIGS. 2 (*a*) and (*b*), composed of POM having an outer diameter of 3.0 mm obtained by continuously forming ink passages 11 of cross-sectional radial inner grooves in an axial direction, and a whole of a coating part 12 which is a tip part is formed by cutting in an approximately shell shape assuming a jet cone shape. Further, the liquid cosmetic compositions of the respective formulations of FIG. 1 were filled in an applicator body (not illustrated) having a valve mechanism, and holes (not illustrated) for introducing the cosmetic composition into a cosmetic passage in an inside of the applicator body are formed at a pen core rear part 10*a* and a pen core side face part 10*b*. The applicator is constituted so that the liquid cosmetic is coated from the coating part by coating operation. A puff used in the comparative example of FIG. 3 is a silicone-made foamed body having a pore of 0.025 to 0.2 μm and a porosity of 80%.

The respective applicators and the like shown in FIG. 1 to FIG. 3 were used to coat the liquid cosmetic on a skin, and the brilliant feeling was functionally evaluated by vision based on the following evaluation criteria.

Evaluation criteria:

A: brilliant feeling is good

B: brilliant feeling is not good that much

C: brilliant feeling is scarce

Measuring method of brilliant feeling of upper and lower:

The applicator was fixed in an upward state and left standing still for one month at room temperature (25° C.). Then, the cosmetic composition was coated by the same method as in the brilliant feeling described above to functionally evaluate the brilliant feeling by vision based on the following evaluation criteria.

Evaluation criteria:

A: brilliant feeling is continued

B: brilliant feeling is low

C: brilliant feeling is scarce

TABLE 1

| | Example No. | | | | | | | | |
|---|---|---|---|---|---|---|---|---|---|
| | 1 | 2 | 3 | 4 | 5 | 6 | 7 | 8 | 9 |
| Water (refined water) | 76.42 | 77.44 | 76.65 | 73.86 | 75.38 | 84.15 | 82.20 | 76.42 | 76.42 |
| 1,3-butylene glycol | 9.56 | 10.47 | 9.57 | 9.30 | 9.63 | 9.63 | 9.63 | 9.56 | 9.56 |
| Acrylic copolymer *1 | 9.27 | 9.27 | 8.96 | 8.96 | 9.27 | 1.51 | 3.45 | 9.27 | 9.27 |
| Carbon black *2 | 2.01 | | 1.94 | 1.94 | 2.01 | 2.01 | 2.01 | 2.01 | 2.01 |
| Surface treated flaky pigment *3 | 0.86 | 0.86 | 0.83 | 4.17 | 0.86 | 0.86 | 0.86 | 0.86 | 0.86 |
| Layered clay mineral particles A *4 | 0.26 | 0.26 | 0.25 | 0.25 | 1.29 | 0.26 | 0.26 | | |
| Layered clay mineral particles B *5 | | | | | | | | 0.26 | |
| Layered clay mineral particles C *6 | | | | | | | | | 0.26 |
| Thickener A (crystalline cellulose) *7 | | | 0.21 | | | | | | |
| Thickener B (dextrin) | | | 0.05 | | | | | | |
| Thickener C (xanthan gum) | | | 0.01 | | | | | | |
| Preservative | 1.17 | 1.25 | 1.09 | 1.08 | 1.11 | 1.13 | 1.14 | 1.17 | 1.17 |
| pH adjusting agent *8 | 0.45 | 0.45 | 0.44 | 0.44 | | 0.45 | 0.45 | 0.45 | 0.45 |
| Total (% by mass) | 100 | 100 | 100 | 100 | 99.55 | 100 | 100 | 100 | 100 |
| *Property | Brush | Brush | Brush | Brush | Brush | Brush | Brush | Brush | Brush |
| Brilliant feeling | A | A | A | A | A | A | A | A | A |
| Upper and lower difference | A | A | A | A | A | A | A | A | A |
| pH of liquid cosmetic composition | 8.2 | 8.4 | 8.3 | 8.3 | 8.4 | 8.2 | 8.2 | 9.5 | 9.5 |
| Viscosity (mPas) | 3.6 | 3.8 | 4.9 | 4.3 | 5.8 | 3.0 | 3.2 | 5.2 | 4.6 |

TABLE 2

| | Comparative Example No. | | | | | | | | |
|---|---|---|---|---|---|---|---|---|---|
| | 1 | 2 | 3 | 4 | 5 | 6 | 7 | 8 | 9 |
| Water (refined water) | 76.42 | 76.42 | 76.42 | 76.42 | 76.68 | 76.68 | 68.19 | 73.94 | 65.03 |
| 1,3-butylene glycol | 9.56 | 9.56 | 9.56 | 9.56 | 9.56 | 9.56 | 8.58 | 9.02 | 9.31 |
| Acrylic copolymer *1 | 9.27 | 9.27 | 9.27 | 9.27 | 9.27 | 9.27 | 8.27 | 9.27 | 20.90 |
| Ca/bon black *2 | 2.01 | 2.01 | 2.01 | 2.01 | 2.01 | 2.01 | 1.79 | | 2.01 |
| Surface treated flaky pigment *3 | 0.86 | 0.86 | 0.86 | | 0.86 | | 11.54 | 0.86 | 0.86 |
| Flaky pigment *9 | | | | 0.86 | | 0.86 | | | |
| Layered clay mineral particles A *4 | 0.26 | 0.26 | 0.26 | 0.26 | | | 0.23 | 5.71 | 0.26 |
| Preservative | 1.17 | 1.17 | 1.17 | 1.17 | 1.17 | 1.17 | 0.99 | 0.75 | 1.17 |
| pH adjusting agent *8 | 0.45 | 0.45 | 0.45 | 0.45 | 0.45 | 0.45 | 0.4 | 0.45 | 0.45 |
| Total (% by mass) | 100 | 100 | 100 | 100 | 100 | 100 | 100 | 100 | 100 |
| *Property | Bulk | Pen core | Puff | Brush | Brush | Brush | Brush | Brush | Brush |
| Brilliant feeling | B | D | B | D | D | B | A | A | B |
| Upper and lower difference | — | A | — | A | C | C | — | — | A |
| pH of liquid cosmetic composition | 8.2 | 8.2 | 8.2 | 8.3 | 8.4 | 8.4 | 8.4 | 8.4 | 8.4 |
| Viscosity (mPas) | 3.6 | 3.6 | 3.6 | 3.9 | 3.8 | 3.8 | 4.8 | 9.4 | 7.1 |

*1 to *9 in Table 1 and Table 2 represent the followings.
*1: Yodosol GH800F, manufactured by Akzo Nobel N.V.; solid content 45%; values in Table 1 and Table 2 were described in terms of a solid content.
*2: DK Black No. 2, manufactured by Daito Kasei Kogyo Co., Ltd.
*3: (production example) product prepared by subjecting Cosmicolor Frost SL (aluminum flake pigment, manufactured by Toyo Aluminum K. K.) to surface treatment by spray-drying of crystalline cellulose (Ceolus RC-591, manufactured by Asahi Kasei Corporation); average particle diameter on a flat surface 10 to 70 μm and a surface cover rate 2%
*4: Kunipia-F, manufactured by Kunimine Industries Co., Ltd.), average particle diameter 700 nm
*5: Sumecton-SWN (manufactured by Kunimine Industries Co., Ltd.), average particle diameter 150 nm
*6: Sumecton-SA (manufactured by Kunimine Industries Co., Ltd.), average particle diameter 350 nm
*7: Crystalline cellulose (Ceolus RC-N30, manufactured by Asahi Kasei Corporation)
*8: AMP, citric acid
*9: Cosmicolor Frost SL (aluminum flake pigment, manufactured by Toyo Aluminum K. K.)

As apparent from the results shown in Table 1 and Table 2 described above, it has been able to confirm that clear and brilliant coating films are easily obtained in Examples 1 to 9 supporting the present disclosure as compared with Comparative Examples 1 to 9 falling out of the present disclosure, while they did not cause the flaky pigments to be overlapped when the liquid cosmetic compositions containing a small amount of the brilliant flaky pigment were filled in an applicator having a coating part composed of a brush and coated on a face to be coated.

In Comparative Examples 7 and 8, the coating films had a brilliant feeling, but the liquids became gradually difficult to be discharged while coating, and the liquids could not be coated (discharged) in evaluation of the upper and lower difference after left standing still for a month.

INDUSTRIAL APPLICABILITY

The liquid cosmetic composition of the present disclosure can be suitably used for liquid eyeliners, liquid eye shadows, eyebrows for drawing lines on eyebrows.

What is claimed is:
1. A liquid cosmetic composition
comprising at least 0.01 to 10 mass % of a flaky pigment having a surface coated with a compound selected from the group consisting of cellulose, hemicellulose, lignin, chitin, and chitosan;
0.05 to 5 mass % of layered clay mineral particles;
1 to 20 mass % in terms of a solid content of an acrylic copolymer; and
water to balance,
wherein the liquid cosmetic is disposed in an applicator having a coating part comprising a brush.
2. The liquid cosmetic composition of claim 1, further comprising a thickener.
3. The liquid cosmetic composition of claim 1, wherein the flaky pigment is an aluminum flake pigment.
4. The liquid cosmetic composition of claim 1, wherein the layered clay mineral particles are layered silicate mineral particles.

* * * * *